(12) United States Patent
Kobayashi et al.

(10) Patent No.: US 7,220,857 B2
(45) Date of Patent: May 22, 2007

(54) AZO DYE COMPOUND

(75) Inventors: Katsumi Kobayashi, Minami-ashigara (JP); Yasuhiro Ishiwata, Minami-ashigara (JP); Kiyoshi Takeuchi, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/280,345

(22) Filed: Nov. 17, 2005

(65) Prior Publication Data

US 2006/0142553 A1 Jun. 29, 2006

(30) Foreign Application Priority Data

Nov. 19, 2004 (JP) ............... 2004-336573

(51) Int. Cl.
    *C09B 17/00* (2006.01)
    *C07D 237/36* (2006.01)
    *C07D 513/04* (2006.01)
    *C07D 487/04* (2006.01)
    *C07D 471/12* (2006.01)

(52) U.S. Cl. .................... 544/234

(58) Field of Classification Search ............ 544/234
    See application file for complete search history.

(56) References Cited

U.S. PATENT DOCUMENTS 4,369,318 A * 1/1983 Jan ................ 544/234

FOREIGN PATENT DOCUMENTS

DE          577631        * 6/1933

OTHER PUBLICATIONS

Beck et al., J. Heterocyclic Chem., 24(1), 243-245, 1987.*

Klaus Hunger (Editor), Industrial Dyes: Chemistry, Properties, Applications (2003) (cover page, colophon, contents (VIII to XI), and pp. 112-117, 134-139, 160-173, and 226-245).

Robert K. Lynn et al.; Toxicology and Applied Pharmacology, vol. 56, pp. 248-258, 1980.

J. Org. Chem., vol. 65, pp. 6388-6397, 2000, Benin et al.

* cited by examiner

*Primary Examiner*—Fiona T. Powers
(74) *Attorney, Agent, or Firm*—Birch, Stewart, Kolasch & Birch, LLP

(57) ABSTRACT

A compound represented by formula (I):

Formula (I)

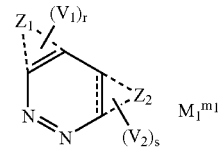

wherein $Z_1$ and $Z_2$ each are atoms necessary for forming an aromatic ring; $V_1$ and $V_2$ each are a substituent $W_1$ or $W_2$; when at least one $V_1$ is $W_1$, at least one $V_2$ is $W_2$, or when at least one $V_1$ is $W_2$, at least one $V_2$ is $W_1$; r is 1 to 4; s is 1 to 4; $M_1$ is a counter ion; $m_1$ is the number necessary for neutralizing charge; $W_1$ is a hydroxyl, primary- or secondary- or tertiary-amino, acylamino, or sulfonamido group; $W_2$ is a nitro, cyano, alkoxycarbonyl, aryloxycarbonyl, alkyl- or aryl-sulfonyl, carbamoyl, sulfamoyl, alkenyl, alkynyl, aryl, heterocyclic, sulfo, carboxyl, heterocyclic oxy, ammonio, alkyl- or aryl-sulfinyl, alkyl- or aryl-sulfonyl, acyl, or aryl- or heterocyclic-azo group; and the aromatic ring may have a substituent other than $V_1$ and $V_2$.

6 Claims, 3 Drawing Sheets

AZO DYE COMPOUND

FIELD OF THE INVENTION

The present invention relates to a compound, which is useful as an azo dye that can be used for dyeing of textile fibers (e.g. cotton, wool, and synthetic fiber), leather, paper, plastic, fur, etc., for food, for a hair dye, for an ink, for inkjet printing, for laser printing, for copying, for image formation by heat-sensitive transfer system, for an optical recording material, for an organic EL luminescent material, for laser, for an organic semiconductor, for a solar cell, for a fluorescent probe, for a nonlinear optical material, for various filters for a solid pickup or camera tube etc., or for a display such as a color liquid crystal display (LCD).

BACKGROUND OF THE INVENTION

Azo dyes have numerous excellent properties such as high dyeing property, fastness to heat, light, and washing, and low production cost, and thus have been hitherto used widely for dyeing of textile fibers (e.g. cotton, wool, and synthetic fiber), leather, paper, plastic, fur, etc., and for food. At present, in addition to those conventional applications, the azo dyes are used for a paint pigment, for an ink, for inkjet printing, for laser printing, for copying, for image formation by heat-sensitive transfer system, for an optical recording material, for an organic EL luminescent material, for laser, for an organic semiconductor, for a solar cell, for a fluorescent probe, for a nonlinear optical material, for various filters for a solid pickup tube etc., for a display such as a color LCD, for a hair dye, and the like. The azo dye has a dye skeleton most widely used. Industrial Dyes: Chemistry, Properties, Applications (edited by K. Hunger, published by Wiley-VCH, 2003) describes extensively specific application examples of the azo dyes.

However, the azo dyes are known to form aromatic amine compounds when they are metabolized reductively in a living body or organisms, and concerns over their safety has been pointed out recently (see R. K. Lynn et al., Toxicol. Appl. Pharmacol., vol. 56, p. 248, 1980, for example). In consideration of influences in a living body, development of hardly reducible azo dyes has been required.

Synthesis of a novel heterocyclic compound having an azo group in a ring, that is, a 1,10-heterodisubstituted benzo[c]cinnoline derivative has been reported recently (see V. Benin et al., J. Org. Chem., vol. 65, p. 6388, 2000, for example). However, the report focuses on a mechanism of a ring formation reaction and discussion of structural chemistry.

SUMMARY OF THE INVENTION

The present invention resides in a compound represented by formula (I):

Formula (I)

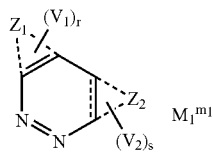

wherein $Z_1$ and $Z_2$ each represent a group of atoms necessary for forming an aromatic ring; $V_1$ and $V_2$ each represent a substituent on the aromatic ring formed by $Z_1$ or $Z_2$; r represents 1 to 4; s represents 1 to 4; the substituents $V_1$ and $V_2$ each represent a substituent represented by $W_1$ or $W_2$ described below; when at least one $V_1$ is a substituent represented by $W_1$, at least one $V_2$ is a substituent represented by $W_2$, or when at least one $V_1$ is a substituent represented by $W_2$, at least one $V_2$ is a substituent represented by $W_1$; $M_1$ represents a counter ion; $m_1$ represents the number necessary for neutralizing charge; $W_1$ represents a hydroxyl group, a primary, secondary or tertiary amino group, an acylamino group, or a sulfonamido group; $W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the aromatic ring formed by $Z_1$ or $Z_2$ may have a substituent other than those represented by $V_1$ and $V_2$.

Further, the present invention resides in an azo dye, which comprises the aforementioned compound.

Other and further features and advantages of the invention will appear more fully from the following description, taken in connection with the accompanying drawings.

DETAILED DESCRIPTION OF THE INVENTION

Figure 1:
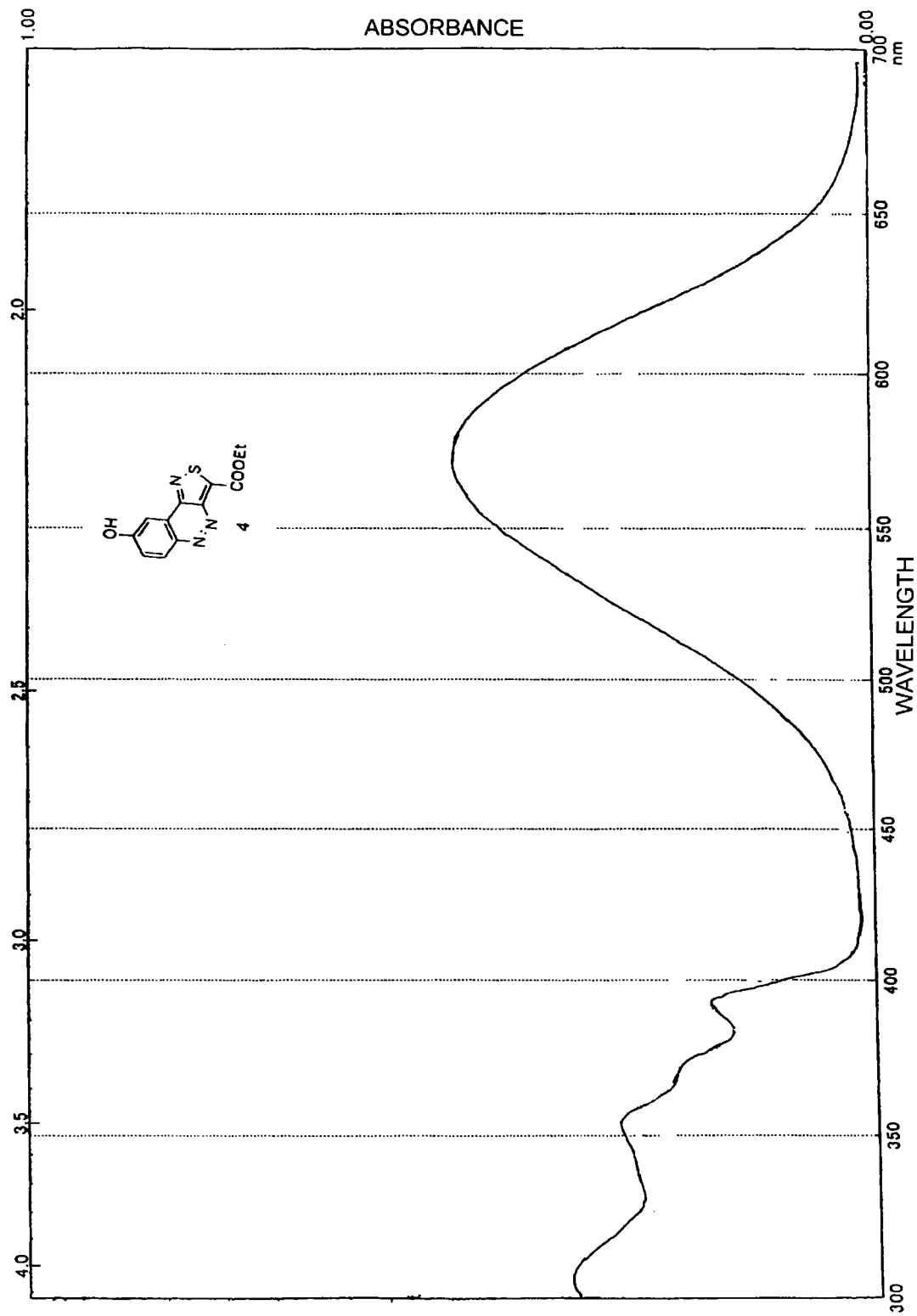
FIG. 1 is an absorption spectrum of Exemplified Compound 4 prepared in Example 1 (N,N-dimethylformamide as a solvent)

According to the present invention, there is provided the following means:

(1) A compound represented by formula (I):

Formula (I)

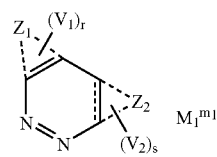

wherein $Z_1$ and $Z_2$ each represent a group of atoms necessary for forming an aromatic ring; $V_1$ and $V_2$ each represent a substituent on the aromatic ring formed by $Z_1$ or $Z_2$; r represents 1 to 4; s represents 1 to 4; the substituents $V_1$ and $V_2$ each represent a substituent represented by $W_1$ or $W_2$ described below; when at least one $V_1$ is a substituent represented by $W_1$, at least one $V_2$ is a substituent represented by $W_2$, or when at least one $V_1$ is a substituent represented by $W_2$, at least one $V_2$ is a substituent represented by $W_1$; $M_1$ represents a counter ion; $m_1$ represents the number necessary for neutralizing charge; $W_1$ represents a hydroxyl group, a primary, secondary or tertiary amino group, an acylamino group, or a sulfonamido group; $W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the aromatic ring formed by $Z_1$ or $Z_2$ may have a substituent other than those represented by $V_1$ and $V_2$.

(2) The compound represented by formula (I) according to the above item (1), which is represented by formula (II):

Formula (II)

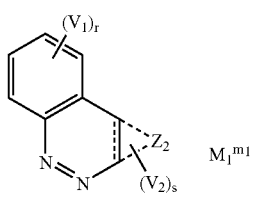

wherein $Z_2$ represents a group of atoms necessary for forming an aromatic ring; $V_1$ and $V_2$ each represent a substituent; r represents 1 to 4; s represents 1 to 4; the substituents $V_1$ and $V_2$ each represent a substituent represented by $W_1$ or $W_2$ described below; when at least one $V_1$ is a substituent represented by $W_1$, at least one $V_2$ is a substituent represented by $W_2$, or when at least one $V_1$ is a substituent represented by $W_2$, at least one $V_2$ is a substituent represented by $W_1$; $M_1$ represents a counter ion; $m_1$ represents the number necessary for neutralizing charge; $W_1$ represents a hydroxyl group, a primary, secondary or tertiary amino group, an acylamino group, or a sulfonamido group; $W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the compound represented by formula (II) may have a substituent other than those represented by $V_1$ and $V_2$.

(3) The compound represented by formula (I) or (II) according to the above item (1) or (2), which is represented by formula (III):

Formula (III)

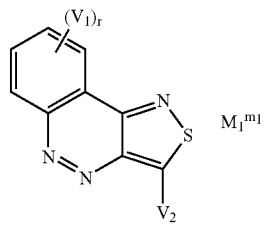

wherein $V_1$ and $V_2$ each represent a substituent; r represents 1 to 4; the substituents $V_1$ and $V_2$ each represent a substituent represented by $W_1$ or $W_2$ described below; when at least one $V_1$ is a substituent represented by $W_1$, $V_2$ is a substituent represented by $W_2$, or when at least one $V_1$ is a substituent represented by $W_2$, $V_2$ is a substituent represented by $W_1$; $M_1$ represents a counter ion; $m_1$ represents the number necessary for neutralizing charge; $W_1$ represents a hydroxyl group, a primary, secondary or tertiary amino group, an acylamino group, or a sulfonamido group; $W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the compound represented by formula (III) may have a substituent other than those represented by $V_1$ and $V_2$.

(4) The compound represented by formula (I) or (II) according to the above item (1) or (2), which is represented by formula (IV):

Formula (IV)

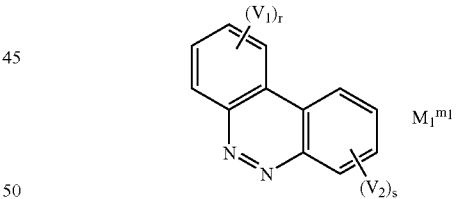

wherein $V_1$ and $V_2$ each represent a substituent; r represents 1 to 4; s represents 1 to 4; the substituents $V_1$ and $V_2$ each represent a substituent represented by $W_1$ or $W_2$ described below; when at least one $V_1$ is a substituent represented by $W_1$, at least one $V_2$ is a substituent represented by $W_2$, or when at least one $V_1$ is a substituent represented by $W_2$, at least one $V_2$ is a substituent represented by $W_1$; $M_1$ represents a counter ion; $m_1$ represents the number necessary for neutralizing charge; $W_1$ represents a hydroxyl group, a primary, secondary or tertiary amino group, an acylamino group, or a sulfonamido group; $W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the compound represented by formula (IV) may have a substituent other than those represented by $V_1$ and $V_2$.

(5) An azo dye comprising the compound according to any one of the above items (1) to (4).

The best mode for carrying out the present invention is described in detail below.

The inventors of the present invention, having conducted extensive studies on development of a hardly reducible azo dye skeleton, succeeded in development of an azo dye stable under reducing conditions, by incorporating an azo group into a ring structure as its part to impart aromaticity. The inventors found that the above-mentioned problems in the conventional technique can be solved, by using a compound represented by formula (I). The present invention has been attained based on the finding.

Next, detailed description will be given of a compound represented by formula (I) according to the present invention.

In the present invention, when a specific moiety is referred to as "group", said moiety means that it per se may be unsubstituted or substituted by one or more (to the greatest possible number of) kinds of substituents. For example, "an alkyl group" means a substituted or unsubstituted alkyl group. A substituent that can be used in the compound of the present invention may be any substituent, regardless of substitution or non-substitution.

Such a substituent is referred to as W, and a substituent represented by W may be any atom or group, which is not particularly limited. Examples of the substituent represented by W include: a halogen atom; an alkyl group (including a cycloalkyl group, a bicycloalkyl group, and a tricycloalkyl group); an alkenyl group (including a cycloalkenyl group and a bicycloalkenyl group); an alkynyl group; an aryl group; a heterocyclic group; a cyano group; a hydroxyl group; a nitro group; a carboxyl group; an alkoxy group; an aryloxy group; a silyloxy group; a heterocyclic oxy group; an acyloxy group; a carbamoyloxy group; an alkoxycarbonyloxy group; an aryloxycarbonyloxy group; an amino group (including an alkylamino group, an arylamino group, and a heterocyclic amino group); an ammonio group; an acylamino group; an aminocarbonylamino group; an alkoxycarbonylamino group; an aryloxycarbonylamino group; a sulfamoylamino group; an alkyl- or aryl-sulfonylamino group; a mercapto group; an alkylthio group; an arylthio group; a heterocyclic thio group; a sulfamoyl group; a sulfo group; an alkyl- or aryl-sulfinyl group; an alkyl- or aryl-sulfonyl group; an acyl group; an aryloxycarbonyl group; an alkoxycarbonyl group; a carbamoyl group; an aryl- or heterocyclic-azo group; an imido group; a phosphino group; a phosphinyl group; a phosphinyloxy group; a phosphinylamino group; a phosphono group; a silyl group; a hydrazino group; a ureido group; a boric acid group (—B(OH)$_2$); a phosphate group (—OPO(OH)$_2$); a sulfate group (—OSO$_3$H); and other known substituents.

Specific examples of W include: a halogen atom (e.g. a fluorine atom, a chlorine atom, a bromine atom, or an iodine atom); an alkyl group [which represents a substituted or unsubstituted linear, branched, or cyclic alkyl group, and which includes an alkyl group (preferably an alkyl group having 1 to 30 carbon atoms, e.g. a methyl group, an ethyl group, an n-propyl group, an isopropyl group, a t-butyl group, an n-octyl group, an eicosyl group, a 2-chloroethyl group, a 2-cyanoethyl group, or a 2-ethylhexyl group), a cycloalkyl group (preferably a substituted or unsubstituted cycloalkyl group having 3 to 30 carbon atoms, e.g. a cyclohexyl group, a cyclopentyl group, or a 4-n-dodecylcyclohexyl group), a bicycloalkyl group (preferably a substituted or unsubstituted bicycloalkyl group having 5 to 30 carbon atoms, i.e. a monovalent group obtained by removing one hydrogen atom from a bicycloalkane having 5 to 30 carbon atoms, e.g. a bicyclo[1,2,2]heptan-2-yl group or a bicyclo[2,2,2]octan-3-yl group), and a tricyclo or higher structure having three or more ring structures; and an alkyl group in a substituent described below (e.g. an alkyl group in an alkylthio group) represents such an alkyl group of the above concept, but it may include an alkenyl group or an alkynyl group]; an alkenyl group [which represents a substituted or unsubstituted linear, branched, or cyclic alkenyl group, and which includes an alkenyl group (preferably a substituted or unsubstituted alkenyl group having 2 to 30 carbon atoms, e.g. a vinyl group, an allyl group, a prenyl group, a geranyl group, or an oleyl group), a cycloalkenyl group (preferably a substituted or unsubstituted cycloalkenyl group having 3 to 30 carbon atoms, i.e. a monovalent group obtained by removing one hydrogen atom from a cycloalkene having 3 to 30 carbon atoms, e.g. a 2-cyclopenten-1-yl group or a 2-cyclohexen-1-yl group), and a bicycloalkenyl group (which represents a substituted or unsubstituted bicycloalkenyl group, preferably a substituted or unsubstituted bicycloalkenyl group having 5 to 30 carbon atoms, i.e. a monovalent group obtained by removing one hydrogen atom from a bicycloalkene having one double bond, e.g. a bicyclo[2,2,1]hept-2-en-1-yl group or a bicyclo[2,2,2]oct-2-en-4-yl group)]; an alkynyl group (preferably a substituted or unsubstituted alkynyl group having 2 to 30 carbon atoms, e.g. an ethynyl group, a propargyl group, or a trimethylsilylethynyl group); an aryl group (preferably a substituted or unsubstituted aryl group having 6 to 30 carbon atoms, e.g. a phenyl group, a p-tolyl group, a naphthyl group, an m-chlorophenyl group, or an o-hexadecanoylaminophenyl group); a heterocyclic group (preferably a monovalent group obtained by removing one hydrogen atom from a substituted or unsubstituted 5- or 6-membered aromatic or nonaromatic heterocyclic compound, which may be condensed with a benzene ring or the like; more preferably a 5- or 6-membered aromatic heterocyclic group having 3 to 30 carbon atoms, e.g. a 2-furyl group, a 2-thienyl group, a 2-pyrimidinyl group, a 2-benzothiazolyl group, or a cationic heterocyclic group, e.g. a 1-methyl-2-pyridinio group or a 1-methyl-2-quinolinio group); a cyano group; a hydroxyl group; a nitro group; a carboxyl group; an alkoxy group (preferably a substituted or unsubstituted alkoxy group having 1 to 30 carbon atoms, e.g. a methoxy group, an ethoxy group, an isopropoxy group, a t-butoxy group, an n-octyloxy group, or a 2-methoxyethoxy group); an aryloxy group (preferably a substituted or unsubstituted aryloxy group having 6 to 30 carbon atoms, e.g. a phenoxy group, a 2-methylphenoxy group, a 4-t-butylphenoxy group, a 3-nitrophenoxy group, or a 2-tetradecanoylaminophenoxy group); a silyloxy group (preferably a silyloxy group having 3 to 20 carbon atoms, e.g. a trimethylsilyloxy group or a t-butyldimethylsilyloxy group); a heterocyclic oxy group (preferably a substituted or unsubstituted heterocyclic oxy group having 2 to 30 carbon atoms, e.g. a 1-phenyltetrazol-5-oxy group or a 2-tetrahydropyranyloxy group); an acyloxy group (preferably a formyloxy group, a substituted or unsubstituted alkylcarbonyloxy group having 2 to 30 carbon atoms, or a substituted or unsubstituted arylcarbonyloxy group having 7 to 30 carbon atoms, e.g. a formyloxy group, an acetyloxy group, a pivaloyloxy group, a stearoyloxy group, a benzoyloxy group, or a p-methoxyphenylcarbonyloxy group); a carbamoyloxy group (preferably a substituted or unsubstituted carbamoyloxy group having 1 to 30 carbon atoms, e.g. an N,N-dimethylcarbamoyloxy group, an N,N-diethylcarbamoyloxy group, a morpholinocarbonyloxy group, an N,N-di-n-octylaminocarbonyloxy group, or an N-n-octylcarbamoyloxy group); an alkoxycarbonyloxy group (preferably a substituted or unsubstituted alkoxycarbonyloxy group having 2 to 30 carbon atoms, e.g. a methoxycarbonyloxy group, an ethoxycarbonyloxy group, a t-butoxycarbonyloxy group, or an n-octylcarbonyloxy group); an aryloxycarbonyloxy group (preferably a substituted or unsubstituted aryloxycarbonyloxy group having 7 to 30 carbon atoms, e.g. a phenoxycarbonyloxy group, a p-methoxyphenoxycarbonyloxy group, or a p-n-hexadecyloxyphenoxycarbonyloxy group); an amino group (preferably an amino group, a substituted or unsubstituted alkylamino group having 1 to 30 carbon atoms, or a substituted or unsubstituted arylamino group having 6 to 30 carbon atoms, e.g. an amino group, a methylamino group, a dimethylamino group, an anilino group, an N-methyl-anilino group, or a diphenylamino group); an ammonio group (preferably an ammonio group, or an ammonio group substituted by a substituted or unsubstituted alkyl group, aryl group, or hetero ring having 1 to 30 carbon atoms, e.g. a trimethylammonio group, a triethylammonio group, or a diphenylmethylammonio group); an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, e.g. a formylamino group, an acetylamino group, a pivaloylamino group, a lauroylamino group, a benzoylamino group, or a 3,4,5-tri-n-octyloxyphenylcarbonylamino group); an aminocarbonylamino group (preferably a substituted or unsubstituted aminocarbonylamino group having 1 to 30 carbon atoms, e.g. a carbamoylamino group, an N,N-dimethylaminocarbonylamino group, an N,N-diethylaminocarbonylamino group, or a morpholinocarbonylamino group); an alkoxycarbonylamino group (preferably a substituted or unsubstituted alkoxycarbonylamino group having 2 to 30 carbon atoms, e.g. a methoxycarbonylamino group, an ethoxycarbonylamino group, a t-butoxycarbonylamino group, an n-octadecyloxycarbonylamino group, or an N-methyl-methoxycarbonylamino group); an aryloxycarbonylamino group (preferably a substituted or unsubstituted aryloxycarbonylamino group having 7 to 30 carbon atoms, e.g. a phenoxycarbonylamino group, a p-chlorophenoxycarbonylamino group, or an m-n-octyloxyphenoxycarbonylamino group); a sulfamoylamino group (preferably a substituted or unsubstituted sulfamoylamino group having 0 to 30 carbon atoms, e.g. a sulfamoylamino group, an N,N-dimethylaminosulfonylamino group, or an N-n-octylaminosulfonylamino group); an alkyl- or aryl-sulfonylamino group (preferably a substituted or unsubstituted alkylsulfonylamino group having 1 to 30 carbon atoms, or a substituted or unsubstituted arylsulfonylamino group having 6 to 30 carbon atoms, e.g. a methylsulfonylamino group, a butylsulfonylamino group, a phenylsulfonylamino group, a 2,3,5-trichlorophenylsulfonylamino group, or a p-methylphenylsulfonylamino group); a mercapto group; an alkylthio group (preferably a substituted or unsubstituted alkylthio group having 1 to 30 carbon atoms, e.g. a methylthio group, an ethylthio group, or an hexadecylthio group); an arylthio group (preferably a substituted or unsubstituted arylthio group having 6 to 30 carbon atoms, e.g. a phenylthio group, a p-chlorophenylthio group, or an m-methoxyphenylthio group); a heterocyclic thio group (preferably a substituted or unsubstituted heterocyclic thio group having 2 to 30 carbon atoms, e.g. a 2-benzothiazolylthio group or a 1-phenyltetrazol-5-ylthio group); a sulfamoyl group (preferably a substituted or unsubstituted sulfamoyl group having 0 to 30 carbon atoms, e.g. an N-ethylsulfamoyl group, an N-(3-dodecyloxypropyl)sulfamoyl group, an N,N-dimethylsulfamoyl group, an N-acetylsulfamoyl group, an N-benzoylsulfamoly group, or an N-(N-phenylcarbamoyl)sulfamoyl group); a sulfo group; an alkyl- or aryl-sulfinyl group (preferably a substituted or unsubstituted alkylsulfinyl group having 1 to 30 carbon atoms, or a substituted or unsubstituted arylsulfinyl group having 6 to 30 carbon atoms, e.g. a methylsulfinyl group, an ethylsulfinyl group, a phenylsulfinyl group, or a p-methylphenylsulfinyl group); an alkyl- or aryl-sulfonyl group (preferably a substituted or unsubstituted alkylsulfonyl group having 1 to 30 carbon atoms, or a substituted or unsubstituted arylsulfonyl group having 6 to 30 carbon atoms, e.g. a methylsulfonyl group, an ethylsulfonyl group, a phenylsulfonyl group, or a p-methylphenylsulfonyl group); an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms and being bonded to said carbonyl group through a carbon atom, e.g. an acetyl group, a pivaloyl group, a 2-chloroacetyl group, a stearoyl group, a benzoyl group, a p-n-octyloxyphenylcarbonyl group, a 2-pyridylcarbonyl group, or a 2-furylcarbonyl group); an aryloxycarbonyl group (preferably a substituted or unsubstituted aryloxycarbonyl group having 7 to 30 carbon atoms, e.g. a phenoxycarbonyl group, an o-chlorophenoxycarbonyl group, an m-nitrophenoxycarbonyl group, or a p-t-butylphenoxycarbonyl group); an alkoxycarbonyl group (preferably a substituted or unsubstituted alkoxycarbonyl group having 2 to 30 carbon atoms, e.g. a methoxycarbonyl group, an ethoxycarbonyl group, a t-butoxycarbonyl group, or an n-octadecyloxycarbonyl group); a carbamoyl group (preferably a substituted or unsubstituted carbamoyl group having 1 to 30 carbon atoms, e.g. a carbamoyl group, an N-methylcarbamoyl group, an N,N-dimethylcarbamoyl group, an N,N-di-n-octylcarbamoyl group, or an N-(methylsulfonyl)carbamoyl group); an aryl- or heterocyclic-azo group (preferably a substituted or unsubstituted aryl azo group having 6 to 30 carbon atoms, or a substituted or unsubstituted heterocyclic azo group having 3 to 30 carbon atoms, e.g. a phenylazo group, a p-chlorophenylazo group, or a 5-ethylthio-1,3,4-thiadiazol-2-ylazo group); an imido group (preferably an N-succinimido group or an N-phthalimido group); a phosphino group (preferably a substituted or unsubstituted phosphino group having 2 to 30 carbon atoms, e.g. a dimethylphosphino group, a diphenylphosphino group, or a methylphenoxyphosphino group); a phosphinyl group (preferably a substituted or unsubstituted phosphinyl group having 2 to 30 carbon atoms, e.g. a phosphinyl group, a dioctyloxyphosphinyl group, or a diethoxyphosphinyl group); a phosphinyloxy group (preferably a substituted or unsubstituted phosphinyloxy group having 2 to 30 carbon atoms, e.g. a diphenoxyphosphinyloxy group or a dioctyloxyphosphinyloxy group); a phosphinylamino group (preferably a substituted or unsubstituted phosphinylamino group having 2 to 30 carbon atoms, e.g. a dimethoxyphosphinylamino group or a dimethylaminophosphinylamino group); a phospho group; a silyl group (preferably a substituted or unsubstituted silyl group having 3 to 30 carbon atoms, e.g. a trimethylsilyl group, a t-butyldimethylsilyl group, or a phenyldimethylsilyl group); a hydrazino group (preferably a substituted or unsubstituted hydrazino group having 0 to 30 carbon atoms, e.g. a trimethylhydrazino group); and a ureido group (preferably a substituted or unsubstituted ureido group having 0 to 30 carbon atoms, e.g. an N,N-dimethylureido group).

Two substituents W in combination may form a ring (an aromatic or nonaromatic hydrocarbon ring, or hetero ring, or a combination thereof forming a polycyclic condensed ring, examples of which include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, or a phenazine ring).

Among the substituents W, with respect to one having a hydrogen atom, the hydrogen atom may be removed and be substituted by any of the above-mentioned substituents. Examples of the substituent W having a hydrogen atom include: a —CONHSO$_2$— group (e.g. a sulfonylcarbamoyl group or a carbonylsulfamoyl group); a —CONHCO— group (e.g. a carbonylcarbamoyl group); and an —SO$_2$NHSO$_2$— group (e.g. a sulfonylsulfamoyl group). Specific examples thereof include: an alkylcarbonylaminosulfonyl group (e.g. an acetylaminosulfonyl group); an arylcarbonylaminosulfonyl group (e.g. a benzoylaminosulfonyl group); an alkylsulfonylaminocarbonyl group (e.g. a methylsulfonylaminocarbonyl group); and an arylsulfonylaminocarbonyl group (e.g. a p-methylphenylsulfonylaminocarbonyl group).

Next, description will be given of the compound represented by formula (I) according to the present invention.

The aromatic ring formed by $Z_1$ or $Z_2$ means an aromatic carbon ring or an aromatic hetero ring. Examples of the aromatic carbon ring formed by $Z_1$ or $Z_2$ include a benzene ring, a naphthalene ring, an anthracene ring, a phenanthrene ring, and a benzene ring to which an aromatic hetero ring described below is condensed by ring condensation. Examples of the aromatic hetero ring formed by $Z_1$ or $Z_2$ include a 5-, 6-, 7-, or 8-membered aromatic hetero ring. A preferred example of the aromatic hetero ring formed by $Z_1$ or $Z_2$ is a 5- or 6-membered nitrogen-containing hetero ring. The 5- or 6-membered nitrogen-containing hetero ring may be any 5- or 6-membered nitrogen-containing hetero ring, and may have a polycyclic heterocyclic structure obtained through ring condensation of a benzene ring or another hetero ring.

The aromatic hetero ring formed by $Z_1$ or $Z_2$ contains a hetero atom. The hetero atom is preferably a nitrogen atom, a sulfur atom, an oxygen atom, a selenium atom, a tellurium atom, a phosphorus atom, a silicon atom, or a boron atom; more preferably a nitrogen atom, a sulfur atom, an oxygen atom, or a selenium atom; particularly preferably a nitrogen atom, a sulfur atom, or an oxygen atom; and most preferably a nitrogen atom or a sulfur atom.

Specific preferred examples of the aromatic hetero ring include a furan ring, a pyrrole ring, a thiophene ring, an imidazole ring, a pyrazole ring, a thiazole ring, an isothiazole ring, an oxazole ring, an isoxazole ring, a triazole ring, a tetrazole ring, a thiadiazole ring, an oxadiazole ring, a pyran ring, a dioxane ring, a pyridine ring, a pyrazine ring, a pyrimidine ring, a pyridazine ring, a thiadiazine ring, an oxadiazine ring, an oxatriazole ring, a thiatriazole ring, an indolizine ring, a ring obtained by subjecting any of the above-mentioned rings to benzo ring condensation, e.g. a benzothiazole ring, a benzoxazole ring, a benzotriazole ring, a benzothiadiazole ring, a benzoxadiazole ring, a pyranone ring, a pyrillium ring, a triazine ring, a tetrazine ring, an indole ring, a quinolizine ring, a quinoline ring, a phthalazine ring, a quinoxaline ring, an isoquinoline ring, a carbazole ring, a phenanthridine ring, a phenanthroline ring, an acridine ring, a purine ring, and a pteridine ring.

Any substituent may be substituted or ring condensed to the above-mentioned hetero rings, and examples of the substituent include those represented by W. A tertiary nitrogen atom in the hetero ring may be substituted, to form into a quaternary nitrogen atom. Note that hetero rings represented by different tautomer structures are all chemically equivalent, which is included in the present invention.

$V_1$ represents a substituent and is preferably substituted onto the aromatic ring formed by $Z_1$. r represents the number of substituents $V_1$, and is preferably 1 to 4, more preferably 1 to 3, and particularly preferably 1 to 2. $V_2$ represents a substituent and is preferably substituted onto the aromatic ring formed by $Z_2$. s represents the number of substituents $V_2$, and is preferably 1 to 4, more preferably 1 to 3, and particularly preferably 1 to 2.

The compound of the present invention is preferably substituted by at least one of $V_1$ and $V_2$, and is more preferably substituted by both $V_1$ and $V_2$.

The substituents $V_1$ and $V_2$ each represent a substituent represented by $W_1$ or $W_2$ described below. When at least one $V_1$ is a substituent represented by $W_1$, at least one $V_2$ is a substituent represented by $W_2$. Alternatively, when at least one $V_1$ is a substituent represented by $W_2$, at least one $V_2$ is a substituent represented by $W_1$.

$W_1$ represents a hydroxyl group, a primary, secondary or tertiary amino group, an acylamino group, or a sulfonamido group (sulfonylamino group). Specific examples of $W_1$ include: a hydroxyl group with a dissociative or undissociative proton; an NH$_2$ group; an alkyl- or aryl-amino group having 1 to 60 carbon atoms (e.g. a methylamino group, an ethylamino group, a propylamino group, a butylamino group, an octylamino group, a dodecylamino group, a benzylamino group, a phenylamino group, or a naphthylamino group); a dialkyl- or diaryl-amino group having 1 to 60 carbon atoms (e.g. a dimethylamino group, a diethylamino group, a dipropylamino group, a dibutylamino group, a dioctylamino group, a didodecylamino group, a dibenzylamino group, an N-butyl-N-ethylamino group, an N-methyl-N-ethylamino group, an N-methyl-N-benzylamino group, a diphenylamino group, a dinaphthylamino group, or an N-(4-tolyl)-N-phenylamino group); an N-alkyl-N-arylamino group having 6 to 60 carbon atoms (e.g. an N-methyl-N-phenylamino group); an acylamino group having 2 to 10 carbon atoms (e.g. an acetylamino group, an n-butanamido group, an octanoylamino group, a benzoylamino group, or a nicotinamido group); and a sulfonamido group having 1 to 60 carbon atoms (e.g. a methanesulfonamido group, a 4-butanesulfonamido group, an 8-octanesulfonamido group, a p-toluenesulfonamido group, a pentafluorobenzenesulfonamido group, or a chlorobenzenesulfonamido group). Any of those groups may further have a substituent such as the substituent W.

Preferred examples of $W_1$ include: a hydroxyl group with a dissociative or undissociative proton; an NH$_2$ group; an alkyl- or aryl-amino group having 1 to 20 carbon atoms (e.g. a methylamino group, an ethylamino group, a propylamino group, a butylamino group, an octylamino group, a dodecylamino group, a benzylamino group, a phenylamino group, or a naphthylamino group); a dialkyl- or diaryl-amino group having 1 to 20 carbon atoms (e.g. a dimethylamino group, a diethylamino group, a dipropylamino group, a dibutylamino group, a dioctylamino group, a didodecylamino group, a dibenzylamino group, an N-butyl-N-ethylamino group, an N-methyl-N-ethylamino group, an N-methyl-N-benzylamino group, a diphenylamino group, a dinaphthylamino group, or an N-(4-tolyl)-N-phenylamino group); an N-alkyl-N-arylamino group having 6 to 20 carbon atoms (e.g. an N-methyl-N-phenylamino group); an acylamino group having 2 to 10 carbon atoms (e.g. an acetylamino group, an n-butanamido group, an octanoylamino group, a benzoylamino group, or a nicotinamido group); and a sulfonamido group having 1 to 20 carbon atoms (e.g. a methanesulfonamido group, a 4-butanesulfonamido group, an 8-octanesulfonamido group, a p-toluenesulfonamido group, a pentafluorobenzenesulfonamido group, or a chlorobenzenesulfonamido group).

More preferred examples of $W_1$ include: a hydroxyl group with a dissociative or undissociative proton; an $NH_2$ group; a substituted or unsubstituted alkylamino group having 1 to 18 carbon atoms; a substituted or unsubstituted dialkyl- or diaryl-amino group having 2 to 18 carbon atoms; a substituted or unsubstituted acylamino group having 2 to 18 carbon atoms; and a substituted or unsubstituted sulfonamido group having 1 to 18 carbon atoms. Further preferred examples of $W_1$ include a hydroxyl group with a dissociative or undissociative proton; an $NH_2$ group, a methylamino group, an ethylamino group, a propylamino group, a butylamino group, an octylamino group, a dimethylamino group, a diethylamino group, a dipropylamino group, a di(2-hydroxyethyl)amino group, a dioctylamino group, a didodecylamino group, a dibenzylamino group, an N-butyl-N-ethylamino group, an N-methyl-N-ethylamino group, an N-methyl-N-benzylamino group, an acetylamino group, an n-butanamido group, a nicotinamido group, a methanesulfonamido group, a 4-butanesulfonamido group, an 8-octanesulfonamido group, a p-toluenesulfonamido group, a pentafluorobenzenesulfonamido group, and a chlorobenzenesulfonamido group.

Particularly preferred examples of $W_1$ include a hydroxyl group with a dissociative or undissociative proton; a dimethylamino group, a methanesulfonamido group, a 4-butanesulfonamido group, a p-toluenesulfonamido group, and a pentafluorobenzenesulfonamido group.

$W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a carboxyl group, a heterocyclic oxy group, an ammonio group, an alkyl- or aryl-sulfinyl group, a sulfo group, an alkyl- or aryl-sulfonyl group, an acyl group, or an aryl- or heterocyclic-azo group. To be specific, $W_2$ represents: a nitro group; a cyano group; an alkenyl group (preferably having 2 to 10 carbon atoms, e.g. a vinyl group, an allyl group, or an oleyl group); an aryl group (preferably having 6 to 20 carbon atoms, e.g. a phenyl group, a p-tolyl group, or a naphthyl group); an acyl group (preferably having 1 to 20 carbon atoms, e.g. an acetyl group, a benzoyl group, a butanoyl group, or a 4-chlorobenzoyl group); a sulfonyl group (preferably having 1 to 20 carbon atoms, e.g. a methanesulfonyl group, a butanesulfonyl group, or a toluenesulfonyl group); an alkyl- or aryl-sulfinyl group (preferably having 1 to 20 carbon atoms, e.g. a methylsulfoxido group, a phenylsulfoxido group, a 4-chlorophenylsulfoxido group, or a 4-nitrophenylsulfoxido group); a carbamoyl group (preferably having 1 to 10 carbon atoms, e.g. an N,N-dimethylcarbamoyl group); a sulfamoyl group (preferably having 0 to 10 carbon atoms, e.g. an N,N-dimethylsulfamoyl group); a sulfo group; a carboxyl group; an alkoxycarbonyl group (preferably having 2 to 20 carbon atoms, e.g. a methoxycarbonyl group, an ethoxycarbonyl group, or a benzyloxycarbonyl group); an aryloxycarbonyl group (preferably having 6 to 20 carbon atoms, e.g. a phenyloxycarbonyl group, a p-tolyloxycarbonyl group, a naphthyloxycarbonyl group, or a p-chlorophenyloxycarbonyl group); or a heterocyclic group (preferably having 0 to 20 carbon atoms, preferably having a hetero atom as a ring forming atom selected from a nitrogen atom, an oxygen atom, and a sulfur atom, and more preferably having a carbon atom as a ring forming atom in addition to the hetero atom, preferably having 3 to 8 members in a ring, and more preferably 5 to 6 members in a ring, e.g. the group represented by W). Note that, $W_2$ may further have a substituent such as the substituent represented by W.

$W_2$ is preferably a nitro group, a cyano group, an aryl group (having 6 to 20 carbon atoms, e.g. a phenyl group, a p-tolyl group, or a naphthyl group), an acyl group (having 1 to 20 carbon atoms, e.g. an acetyl group, a benzoyl group, a butanoyl group, or a 4-chlorobenzoyl group), a sulfonyl group (having 1 to 20 carbon atoms, e.g. a methanesulfonyl group, a butanesulfonyl group, or a toluenesulfonyl group), an alkyl- or aryl-sulfinyl group (having 1 to 20 carbon atoms, e.g. a methylsulfoxido group, a phenylsulfoxido group, a 4-chlorophenylsulfoxido group, or a 4-nitrophenylsulfoxido group), a carbamoyl group (having 1 to 10 carbon atoms, e.g. an N,N-dimethylcarbamoyl group), a sulfamoyl group (having 0 to 10 carbon atoms, e.g. an N,N-dimethylsulfamoyl group), an alkoxycarbonyl group (having 2 to 20 carbon atoms, e.g. a methoxycarbonyl group, an ethoxycarbonyl group, or a benzyloxycarbonyl group), or an aryloxycarbonyl group (having 6 to 20 carbon atoms, e.g. a phenyloxycarbonyl group, a p-tolyloxycarbonyl group, a naphthyloxycarbonyl group, or a p-chlorophenyloxycarbonyl group).

$W_2$ more preferably represents a nitro group, a cyano group, an alkoxycarbonyl group (having 2 to 20 carbon atoms, e.g. a methoxycarbonyl group, an ethoxycarbonyl group, or a benzyloxycarbonyl group), an aryloxycarbonyl group (having 6 to 20 carbon atoms, e.g. a phenyloxycarbonyl group, a p-tolyloxycarbonyl group, a naphthyloxycarbonyl group, or a p-chlorophenyloxycarbonyl group), an alkyl- or aryl-sulfonyl group, a carbamoyl group, a sulfamoyl group, or an acyl group.

$W_2$ is particularly preferably a cyano group, a methoxycarbonyl group, an ethoxycarbonyl group, a benzyloxycarbonyl group, a phenyloxycarbonyl group, a p-tolyloxycarbonyl group, a naphthyloxycarbonyl group, a p-chlorophenyloxycarbonyl group, a methylsulfonyl group, a carbamoyl group, a sulfamoyl group, or an acyl group.

The aromatic hetero ring formed by $Z_1$ or $Z_2$ may further have a substituent other than the substituents represented by $V_1$ and $V_2$. Examples thereof include the substituent represented by W.-

$M_1$ represents a cation or an anion necessary for neutralizing the charge of the compound molecule. The anion may be an inorganic anion or an organic anion, and examples thereof include: a halide anion (e.g. a fluoride ion, a chloride ion, or an iodide ion); a substituted arylsulfonate ion (e.g. a p-toluenesulfonate ion or a p-chlorobenzenesulfonate ion); an aryldisulfonate ion (e.g. a 1,3-benzenedisulfonate ion, a 1,5-naphthalenedisulfonate ion, or a 2,6-naphthalenedisulfonate ion); an alkylsulfate ion (e.g. a methylsulfate ion); a sulfate ion; a thiocyanate ion; a perchlorate ion; a tetrafluoroborate ion; a picrate ion; an acetate ion; and a trifluoromethanesulfonate ion. Further, an ionic polymer may be used. $CO_2^-$ and $SO_3^-$ each having a hydrogen ion as a counter ion may be represented as $CO_2H$ and $SO_3H$, respectively. Typical examples of the cation include: inorganic cations, e.g. a hydrogen ion ($H^+$), an alkali metal ion (e.g. a sodium ion, a potassium ion, or a lithium ion), and an alkali earth metal ion (e.g. a calcium ion); and organic ions, e.g. an ammonium ion (e.g. an ammonium ion, a tetraalkylammonium ion, a triethylammonium ion, a pyridinium ion, an ethylpyridinium ion, or a 1,8-diazabicyclo[5.4.0]-7-undecenium ion).

$m_1$ represents the number of cations or anions necessary for neutralizing the charge. $m_1$ may be 0 when neutralization is not necessary, and $m_1$ is preferably 0 to 10.

Next, description will be given of a compound represented by formula (II), (III), or (IV) according to the present invention.

In formulae (II), (III), and (IV), $Z_2$, $V_1$, $V_2$, $M_1$, and $m_1$ each have the same meanings as those in formula (I).

The compound of the present invention, represented by formula (I), (II), (III) or (IV), may preferably be used as an azo dye.

Intramolecular azo bond in formula (I), (II), (III) or (IV) may be formed, for example, through a method involving intramolecular azo coupling of a bi(hetero)aryl compound having an amino group (e.g. a method of forming the bond, according to the description by V. Benin et al., in J. Org. Chem., vol. 65, p. 6388, 2000) or a method of forming the bond through a reaction between an amino group on a bi(hetero)aryl compound and a nitrogen-containing compound (e.g. a method of forming the bond through a reaction between the amino group and a nitrite in the presence of an acid). A method of preparing the bi(hetero)aryl compound having an amino group may be determined, according to a target compound structure having the substituents $V_1$ and $V_2$.

The substituents $V_1$ and $V_2$ may be introduced at any time in a reaction process, and are preferably introduced before the intramolecular azo coupling is performed. For introducing the substituents $V_1$ and $V_2$ at the beginning or during the reaction process, the substituents are arbitrarily protected or deprotected, to thereby obtain a compound having the target structure.

Next, specific particularly preferred examples among the compounds of the present invention as described in detail in the above description of the best mode for carrying out the invention will be shown, but the present invention is not limited thereto. Note that Me and Et in structural formulae represent a methyl group and an ethyl group, respectively.

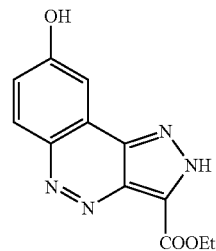

1

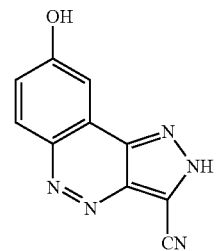

2

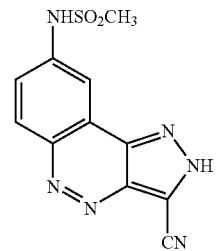

3

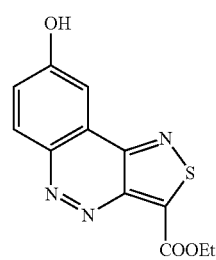

4

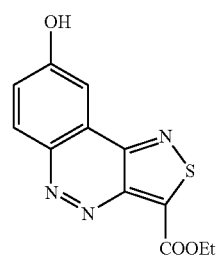

5

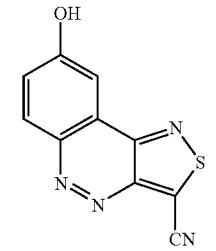

6

-continued

-continued

-continued

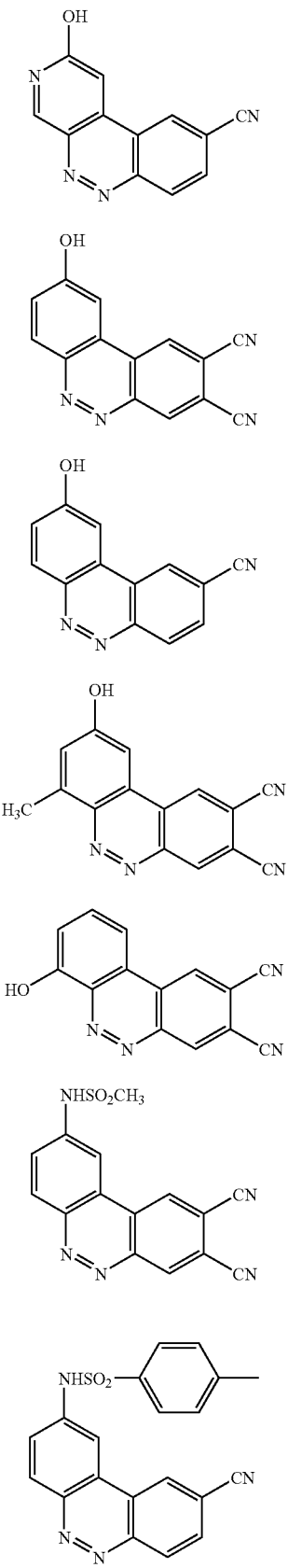

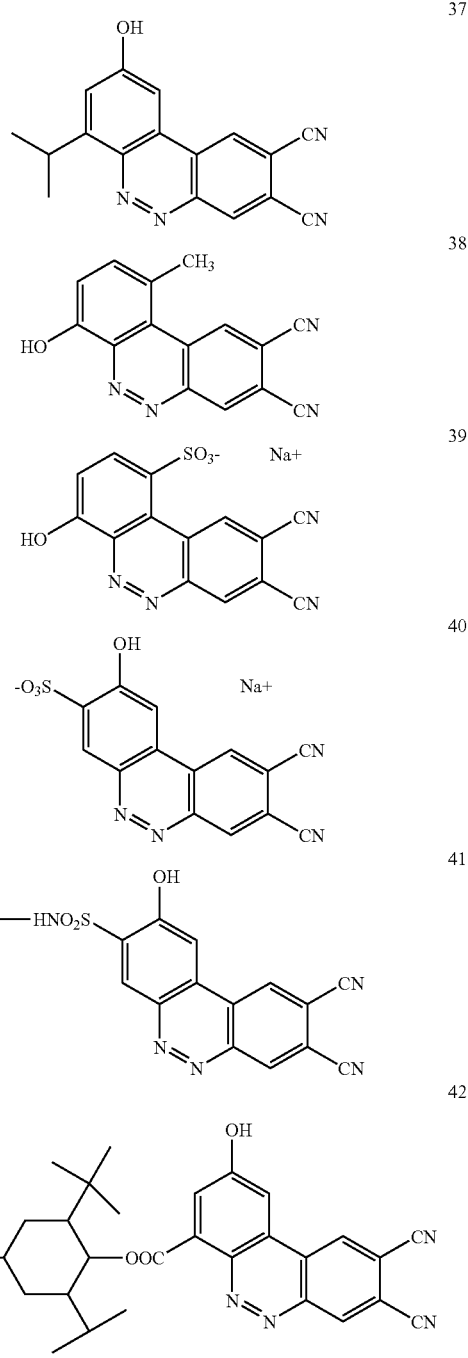

In the case where the compound of the present invention has a plurality of asymmetric carbon atoms in the molecule, a plurality of stereoisomers exist for the same structure. In this connection, in the specification, the compound of the present invention is shown to include all the possible stereoisomers. In the present invention, only one of the above plurality of stereoisomers may be used, or alternatively two or more stereoisomers may be used as a mixture.

The compound of the present invention can be preferably used as a dye that can be used for dyeing textile fibers (e.g. cotton, wool, or synthetic fiber), leather, paper, plastic, fur, etc., for food, for a hair dye (e.g. a permanent-, semi-permanent-, or temporary hair color), for an ink, for inkjet printing, for laser printing, for copying, for image formation by heat-sensitive transfer system, for an optical recording material, for an organic EL (electroluminescent) light-emitting material, for laser, for an organic semiconductor, for a solar cell, for a fluorescent probe, for a nonlinear optical material, for various filters for a solid state pickup tube, etc., or for a display (e.g. a color LCD).

According to the present invention, there can be provided a compound, which is useful as an azo dye, which is stable under reducing conditions, and which is improved in influence in a living body, as well as an azo dye can be provided.

The novel compound of the present invention exhibits, in addition to the above, high dyeing property, coloring property, and fastness, and further it can realize low production cost. The compound serves as an azo dye, to provide those effects.

The present invention will be described in more detail based on the following examples, but the invention is not intended to be limited thereto.

EXAMPLES

Example 1

Synthesis of Exemplified Compound 4

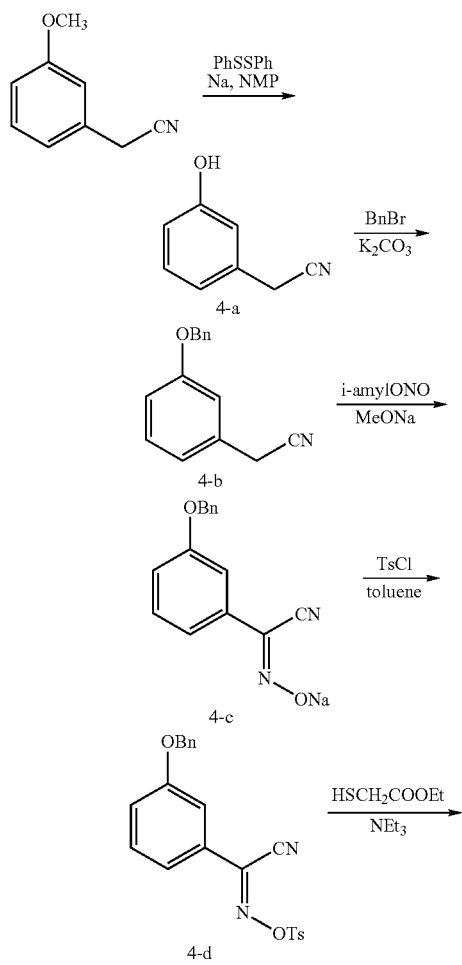

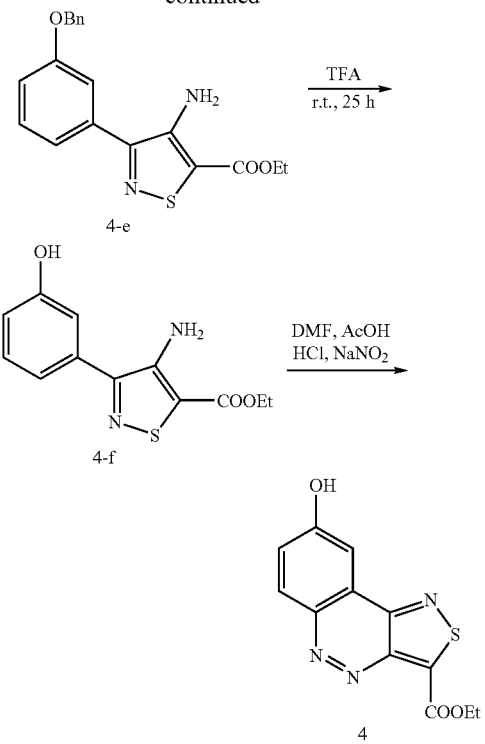

(A) Synthesis of Compound 4-a

In a nitrogen atmosphere, 15.5 g of metallic sodium, 200 ml of 1-methyl-2-pyrrolidinone (NMP), and 66.8 g of diphenyldisulfide (PhSSPh) were placed into a flask, and the mixture was refluxed under heating at an outside temperature of 200° C. for 30 minutes. Thereto, added was a solution prepared by dissolving 75 g of (3-methoxyphenyl)acetonitrile in 200 ml of 1-methyl-2-pyrrolidinone, while being refluxed at the same temperature, followed by refluxing under heating at an outside temperature of 200° C. for additional 3 hours. After completion of the reaction, the reaction liquid was cooled to room temperature (r.t.), and 200 ml of hexane and 400 ml of a 0.5M aqueous sodium hydroxide solution were added thereto. The resultant mixture was stirred and transferred into a separatory funnel, and the resultant hexane layer was separated and removed. To the obtained aqueous layer, was added 3M hydrochloric acid to adjust the solution to be acidic, and was subjected to extraction by ethyl acetate. The solution was separated, and an ethyl acetate layer was obtained. The ethyl acetate layer was washed with 1M hydrochloric acid and then a saturated saline solution, dried over anhydrous magnesium sulfate, followed by distilling off the solvent, and being purified by silica gel column chromatography, to thereby obtain 70.4 g (100% yield) of Compound 4-a.

$^1$H NMR (300 MHz, CDCl$_3$) δ (ppm): 3.73 (2H, s), 6.16 (1H, s), 6.80 to 6.89 (3H, m), 7.20 to 7.30 (1H, m)

(B) Synthesis of Compound 4-b 20 g of Compound 4-a, 27 g of benzyl bromide, and 25 g of potassium carbonate were stirred in 100 ml of DMF at an outside temperature of 60° C. for 3 hours. The reaction liquid was cooled, and 200 ml of ethyl acetate and 200 ml of 1M hydrochloric acid were added thereto. The mixture was stirred, and an organic layer was separated. The organic layer was washed with 1M hydrochloric acid and then a saturated saline solution, dried over anhydrous magnesium sulfate, followed by distilling off the solvent, and being purified by silica gel column chromatography, to thereby obtain 20.8 g (62% yield) of Compound 4-b.

$^1$H NMR (300 MHz, CDCl$_3$) δ (ppm): 3.70 (2H, s), 5.08 (2H, s), 6.88 to 6.95 (3H, m), 7.23 to 7.45 (6H, m)

(C) Synthesis of Compound 4-c 18.5 g of sodium methoxide and 250 ml of ethanol were mixed, and the mixture was cooled to an outside temperature of −30° C. and stirred. Thereto, was added dropwise slowly a 150 ml ethanoL solution containing 85 g of Compound 4-b and 48 ml of isoamyl (i-amyl) nitrite, under cooling at an outside temperature of −30° C., while an inside temperature Was maintained at −25° C. or lower. After completion of the dropwise addition, the mixture was stirred at an outside temperature of −30° C. for 1 hour, and then at room temperature for 1 hour. Then, the reaction liquid was concentrated by using a rotary evaporator. Thereto, 200 ml of ether was added, and the whole was stirred at room temperature. 200 ml of ethyl acetate was added to crystals collected through filtration, and the mixture was stirred at room temperature for 20 minutes. The crystals were collected through filtration, washed with ethyl acetate, and dried, to thereby obtain 68 g (65% yield) of Compound 4-c.

$^1$H NMR (300 MHz, DMSO-d$_6$) δ (ppm): 5.12 (2H, s), 6.70 to 6.78 (1H, dd, J=9 Hz, J=1.5 Hz), 7.08 to 7.23 (2H, m), 7.28 to 7.50 (6H, m)

(D) Synthesis of Compound 4-d 67 g of Compound 4-c and 48 g of p-toluenesulfonyl chloride in 500 ml of toluene were refluxed under heating for 3 hours. The reaction liquid was cooled, and then 300 ml of water and 100 ml of ethyl acetate were added thereto for extraction by ethyl acetate. An organic layer was dried, concentrated, and purified by silica gel chromatography, to thereby obtain 43 g (53% yield) of Compound 4-d.

$^1$H NMR (300 MHz, CDCl$_3$) δ (ppm): 5.10 (2H, s), 7.12 to 7.18 (1H, m), 7.35 to 7.43 (11H, m), 7.91 to 7.95 (2H, d, J=8 Hz)

(E) Synthesis of Compound 4-e 11.6 g of Compound 4-d was stirred and dissolved in 100 ml of ethanol. 5.06 g of ethyl thioglycolate was added thereto, and the whole was stirred and mixed at room temperature. 5.4 ml of triethylamine was added dropwise slowly into the mixture under stirring and cooling at an outside temperature of 0° C. After completion of the dropwise addition, the mixture was heated to room temperature and stirred for additional 1 hour. 1M hydrochloric acid and ethyl acetate were added to the reaction liquid, for extraction by ethyl acetate. An organic layer was washed successively with a 0.5M aqueous sodium hydroxide solution, 1M hydrochloric acid, and a saturated saline solution, dried over magnesium sulfate, and concentrated, and purified by silica gel column chromatography, to thereby obtain 7.7 g (62% yield) of Compound 4-e.

$^1$H NMR (300 MHz, CDCl$_3$) δ (ppm): 1.38 to 1.42 (3H, t, J=7 Hz), 4.34 to 4.39 (2H, d, J=7 Hz), 5.12 (2H, s), 5.36 (2H, s), 7.05 to 7.09 (1H, m), 7.30 to 7.49 (8H, m)

(F) Synthesis of Compound 4-f 7.7 g of Compound 4-e was stirred in 50 ml of trifluoroacetic acid (TFA) for 10 hours. Water and ethyl acetate were added to the reaction liquid, for extraction by ethyl acetate. An organic layer was washed successively with water and a saturated saline solution, dried over magnesium sulfate, and concentrated, and purified by silica gel column chromatography, to thereby obtain 3.7 g (64% yield) of Compound 4-f.

$^1$H NMR (300 MHz, CDCl$_3$) δ (ppm): 1.37 to 1.40 (3H, t, J=7 Hz), 4.34 to 4.39 (2H, d, J=7 Hz), 5.1 to 5.7 (2H, broad), 6.90 to 6.95 (1H, d, J=8 Hz), 7.1 to 7.3 (3H, m), 7.35 to 7.39 (1H, t, J=8 Hz)

(G) Synthesis of Compound 4

3.6 g of Compound 4-f, 10 ml of DMF, 40 ml of acetic acid (AcOH), 5 ml of water, and 15 ml of concentrated hydrochloric acid (c. HCl) were mixed, and the mixture was cooled under stirring in a salt-ice water bath to an inside temperature of 0° C. 1.4 g of sodium nitrite as a solid was added slowly to the mixture under stirring at an inside temperature of 0° C. The mixture was stirred at the same temperature for additional 1 hour, and the reaction liquid was poured into 200 ml of water. Precipitated crystals were collected through filtration. The crystals were added to 70 ml of methanol, and 3 ml of triethylamine was added thereto. The mixture was stirred to dissolve the crystals, and impurities were removed through filtration. Then, 7 ml of acetic acid was added to the filtrate under stirring, to precipitate crystals. The crystals were collected through filtration, washed with running methanol, and dried, to thereby obtain 1.0 g (36% yield) of Compound 4. Compound 4 had a melting point of 251 to 253° C.

FIG. 1 shows an absorption spectrum of the thus-obtained Compound 4. As is apparent from FIG. 1, Compound 4 in a solution containing 3 drops of 1,8-diazabicyclo[5.4.0]-7-undecene (DBU) in N,N-dimethylformamide (DMF) had λmax (maximum absorption wavelength) of 573.3 nm, and εmax (maximum molar absorption coefficient) of $1.46×10^4$ cm$^{-1}$M$^{-1}$.

The NMR spectrum of Compound 4 was as described below.

$^1$H NMR (300 MHz, DMSO-d$_6$) δ (ppm): 1.40 to 1.45 (3H, t, J=7 Hz), 4.50 to 4.57 (2H, d, J=7 Hz), 7.17 (1H, s), 7.50 to 7.56 (1H, dd, J=8 Hz, J=1.5 Hz), 7.83 to 7.85 (1H, d, J=1.5 Hz), 8.58 to 8.63 (1H, d, J=8 Hz)

Example 2

Synthesis of Exemplified Compound 31

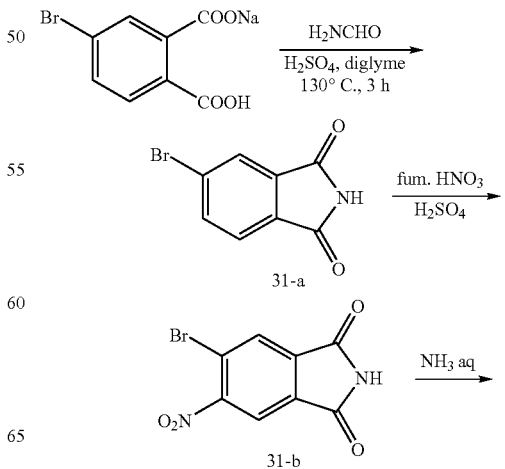

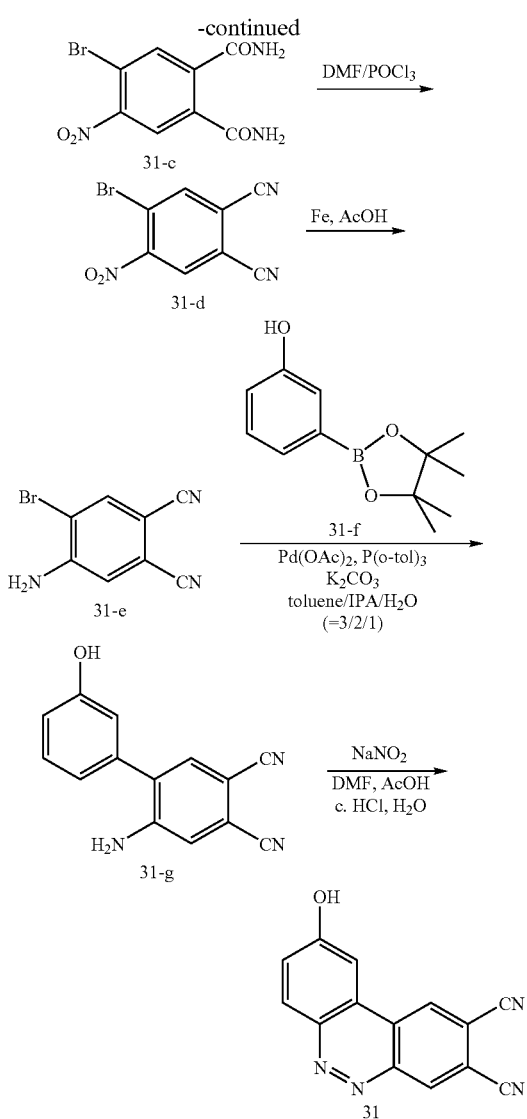

(A) Synthesis of Compound 31-a 700 g of monosodium 4-bromophthalate, 590 g of formamide, 89 ml of concentrated sulfuric acid, and 360 ml of diglyme were placed into a 3 L three-necked flask, and the mixture was stirred under heating at an inside temperature of 130 to 140° C. for 7 hours. After cooling of the mixture to room temperature, 930 ml of DMF and 460 ml of water were added thereto, and the mixture was stirred at room temperature for 2 hours. Crystals were collected through filtration and added to 1.5 L of isopropyl alcohol. The resultant was refluxed under heating for 30 minutes, and then stirred at room temperature for 3 hours. The crystals were collected through filtration, washed with running hexane, and dried, to thereby obtain 563 g (95% yield) of Compound 31-a.

(B) Synthesis of Compound 31-c 194 ml of fuming nitric acid (fum. $HNO_3$) was added to 0.9 L of concentrated sulfuric acid under stirring and cooling in an ice water bath. The mixture was stirred for 1 hour under cooling in an ice water bath, and then 215 g of Compound 31-a was added slowly to the mixture in portions over 30 minutes, while an inside temperature was maintained at 15° C. or lower. After completion of the addition, the mixture was stirred at room temperature for 8 hours. The reaction liquid was poured into 1 L of ice water, to precipitate crystals. After stirring, the crystals were collected through filtration, and washed with running water. The thus-obtained crude crystals of Compound 31-b were transferred to another flask without purification. 1 L of DMF was added thereto, and the whole was stirred at room temperature. To the resultant suspension, 200 ml of 25% ammonia water was added under stirring, and the mixture was stirred at room temperature for 3 hours. The crystals were collected through filtration, and added to 1.5 L of isopropyl alcohol. The mixture was refluxed under heating for 30 minutes, and then stirred at room temperature for 3 hours. The crystals were collected through filtration, washed with running hexane, and dried, to thereby obtain 131 g (48% yield from Compound 31-a) of Compound 31-c.

(C) Synthesis of Compound 31-d 150 g of Compound 31-c was dissolved in 300 ml of DMF, and 200 g of phosphorus oxychloride was added dropwise to the mixture under stirring and cooling in an ice water bath over 1 hour. After completion of the dropwise addition, the phosphorus oxychloride was further dissolved, and the mixture was stirred for 2 hours under cooling in an ice water bath. The reaction liquid was poured slowly into 1.5 L of water, to precipitate crystals. After stirring, the crystals were collected through filtration. The crystals were dissolved in 500 ml of ethyl acetate, dried over anhydrous magnesium sulfate, and filtrated, and the ethyl acetate solution was concentrated. 300 ml of hexane was added to the thus-obtained slurry, and the mixture was stirred, followed by leaving to stand overnight. The thus-obtained crystals were collected through filtration, and dried, to thereby obtain 89 g (68% yield) of Compound 31-d.

$^1$H NMR (300 MHz, $CDCl_3$) δ (ppm): 8.22 (1H, s), 8.25 (1H, s)

(D) Synthesis of Compound 31-e 37.3 g of reduced iron and 200 ml of acetic acid were stirred at room temperature. 44.3 g of Compound 31-d was added slowly thereto in portions, while an inside temperature was maintained at 60° C. or lower. After completion of the addition, the mixture was stirred at room temperature for 1 hour. The reaction liquid was poured into 1 L of water, and the whole was stirred at room temperature. Crystals obtained through filtration were dissolved in 500 ml of DMF, and then passed through cerite for filtration. The thus-obtained filtrate was poured into water, and the whole was stirred, to thereby collect crystals through filtration. 1 L of acetone was added to the crystals, and the mixture was stirred under heating, to completely dissolve the crystals. Then, impurities were removed through filtration. The filtrate was concentrated to a volume of about 150 ml, and left standing. The thus-precipitated crystals were collected through filtration, and dried, to thereby obtain 25 g (64% yield) of Compound 31-e.

$^1$H NMR (300 MHz, DMSO-$d_6$) δ (ppm): 6.85 to 6.94 (2H, broad), 7.19 (1H, s), 8.17 (1H, s)

(E) Synthesis of Compound 31-g

In a nitrogen atmosphere, 2.2 g of Compound 31-e, 2.2 g of commercially available Compound 31-f, 2.8 g of potassium carbonate, 0.112 g of palladium acetate, 0.304 g of tri(o-tolyl)phosphine, 15 ml of toluene, 5 ml of water, and 10 ml of IPA were mixed, and the mixture was stirred under heating at an outside temperature of 80° C. for 4 hours. To the reaction liquid, 1M hydrochloric acid and ethyl acetate were added, for extraction by ethyl acetate. The resultant organic layer was washed with a saturated saline solution, dried over magnesium sulfate, and concentrated, and purified by silica gel column chromatography, to thereby obtain 1.66 g (71% yield) of Compound 31-g.

$^1$H NMR (300 MHz, DMSO-d$_6$) δ (ppm): 6.3 to 6.4 (2H, broad), 6.78 to 6.83 (3H, m), 7.18 (1H, s), 7.29 to 7.33 (1H, t, J=8 Hz), 7.57 (1H, s), 9.67(1H, s)

(F) Synthesis of Compound 31

6.0 g of Compound 31-g, 30 ml of DMF, 120 ml of AcOH, 20 ml of water, and 30 ml of c. HCl were mixed, and the mixture was stirred under cooling in a salt-ice water bath to an inside temperature of 0° C. 5.3 g of sodium nitrite as a solid was added slowly to the mixture under stirring at an inside temperature of 0° C. The mixture was stirred at the same temperature for additional 0.5 hour, and the reaction liquid was poured into 500 ml of water. Precipitated crystals were collected through filtration. The crystals were added to 70 ml of methanol, and 3 ml of triethylamine was added thereto. The mixture was stirred to dissolve the crystals, and impurities were removed through filtration. Then, 7 ml of acetic acid was added to the filtrate under stirring, to precipitate crystals. The crystals were collected through filtration, washed with running methanol, and dried, to thereby obtain 4.62 g (74% yield) of Compound 31. Compound 31 had a melting point of 300° C. or higher.

Figure 2:
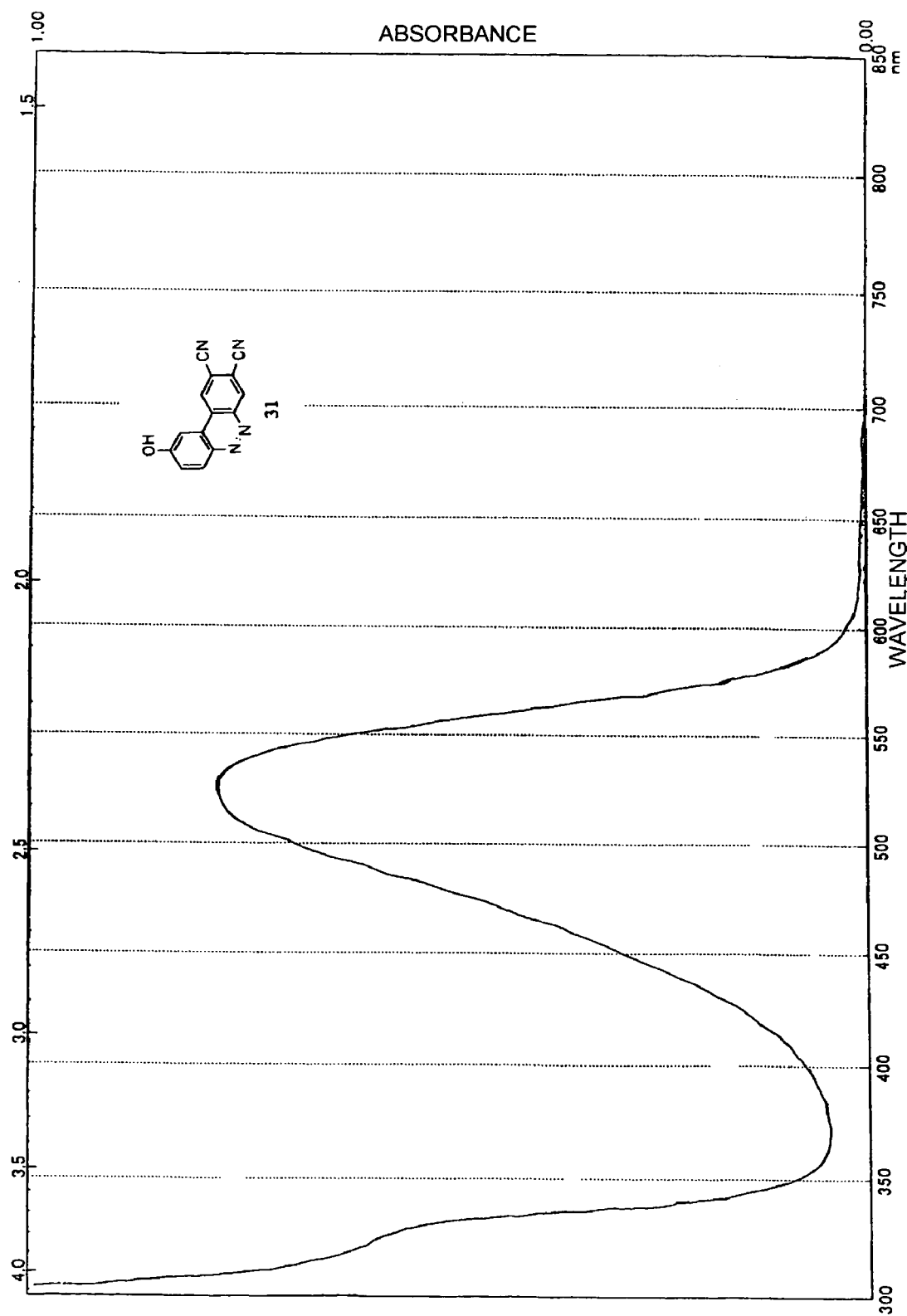
FIG. 2 is an absorption spectrum of Exemplified Compound 31 prepared in Example 2 (N,N-dimethylformamide as a solvent)

FIG. 2 shows an absorption spectrum of the thus-obtained Compound 31. As is apparent from FIG. 2, Compound 31 in a solution containing 3 drops of DBU in DMF had λmax of 524.4 nm, and εmax of 1.89×10$^4$ cm$^{-1}$M$^{-1}$.

The MS spectrum of Compound 31 was as described below. MS (negative) m/z 245 (M–H)$^-$ Example 3

Synthesis of Exemplified Compound 33

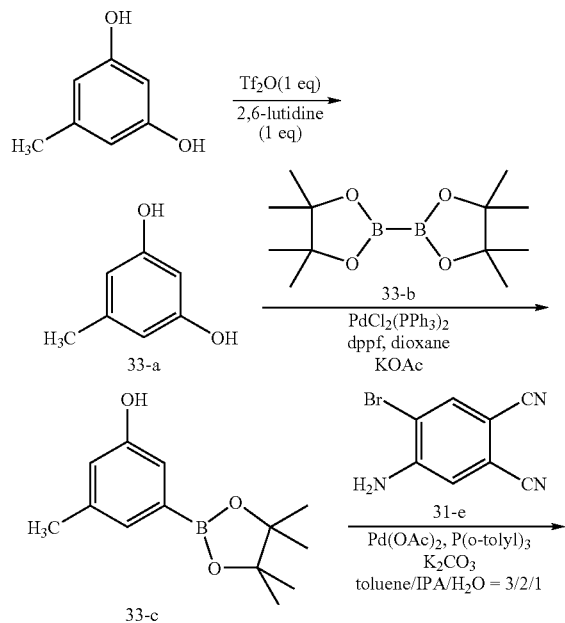

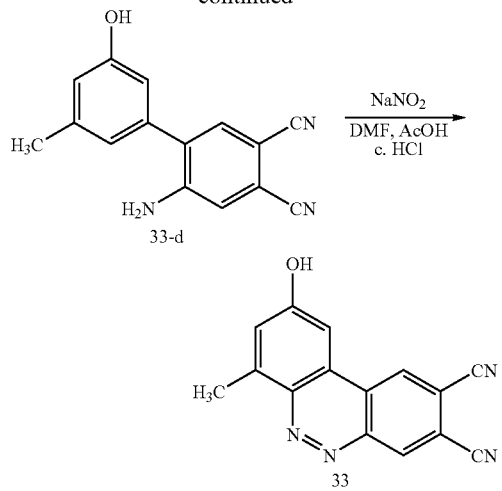

(A) Synthesis of Compound 33-a 11 g of 5-methylresorcinol was dissolved in 100 ml of methylene chloride. 25 g of trifluoromethanesulfonic anhydride, 11.3 ml of 2,6-lutidine, and 0.2 g of 4-dimethylaminopyridine (DMAP) were added successively, to the mixture, under cooling in an ice water bath, and the resultant mixture was stirred at room temperature for 3 hours. A saturated aqueous ammonium chloride solution and ethyl acetate were added to the reaction liquid, for extraction by ethyl acetate. An organic layer was washed with a saturated saline solution, dried over magnesium sulfate, and concentrated, and purified by silica gel column chromatography, to thereby obtain 3.15 g (15% yield) of Compound 33-a.

$^1$H NMR (300 MHz, CDCl$_3$) δ (ppm): 2.34 (3H, s), 6.18 (1H,s), 6.61 (1H,s), 6.67 (1H,s), 6.70 (1H,s)

(B) Synthesis of Compound 33-c

In a nitrogen atmosphere, 5.45 g of commercially available Compound 33-b, 1.3 g of dichlorobistriphenylphosphine palladium, 1.08 g of bisdiphenylphosphinoferrocene (dppf), 5.75 g of potassium acetate, 50 ml of dioxane, and 5.0 g of Compound 33-a were mixed, and the mixture was stirred at an outside temperature of 80° C. for 3 hours. A saturated aqueous ammonium chloride solution and ethyl acetate were added to the reaction liquid, for extraction by ethyl acetate. An organic layer was washed with a saturated saline solution, dried over magnesium sulfate, and concentrated, and purified by silica gel column chromatography, to thereby obtain 3.1 g (68% yield) of Compound 33-c.

$^1$H NMR (300 MHz, CDCl$_3$) δ (ppm): 1.34 (12H, s), 2.30 (3H, s), 4.88 (1H,s), 6.79 (1H,s), 7.08 (1H,s), 7.25 (1H,s)

(C) Synthesis of Compound 33-d

In a nitrogen atmosphere, 3.1 g of Compound 33-c, 2.94 g of Compound 31-e, 3.65 g of potassium carbonate, 0.15 g of palladium acetate, 0.4 g of tri(o-tolyl)phosphine, 15 ml of toluene, 5 ml of water, and 10 ml of isopropyl alcohol were mixed, and the mixture was stirred at an outside temperature of 80° C. for 3 hours. 1M hydrochloric acid and ethyl acetate were added to the reaction liquid, for extraction by ethyl acetate. An organic layer was washed with a saturated saline solution, dried over magnesium sulfate, and concentrated, and purified by silica gel column chromatography, to thereby obtain 2.45 g (74% yield) of Compound 33-d.

(D) Synthesis of Compound 33

2.4 g of Compound 33-d, 15 ml of DMF, 50 ml of AcOH, 7 ml of water, and 10 ml of c. HCl were mixed, and the mixture was stirred under cooling in a salt-ice water bath to an inside temperature of 0° C. 1.46 g of sodium nitrite as a solid was added slowly to the mixture under stirring at an inside temperature of 0° C. The mixture was stirred at the same temperature for additional 0.5 hour, and the reaction liquid was poured into 200 ml of water. Precipitated crystals were collected through filtration. The crystals were added to 70 ml of methanol, and 3 ml of triethylamine was added thereto. The mixture was stirred to dissolve the crystals, and impurities were removed through filtration. Then, 7 ml of acetic acid was added to the filtrate under stirring, to precipitate crystals. The crystals were collected through filtration, washed with running methanol, and dried, to thereby obtain 1.7 g (68% yield) of Compound 33. Compound 33 had a melting point of 300° C. or higher.

Figure 3:
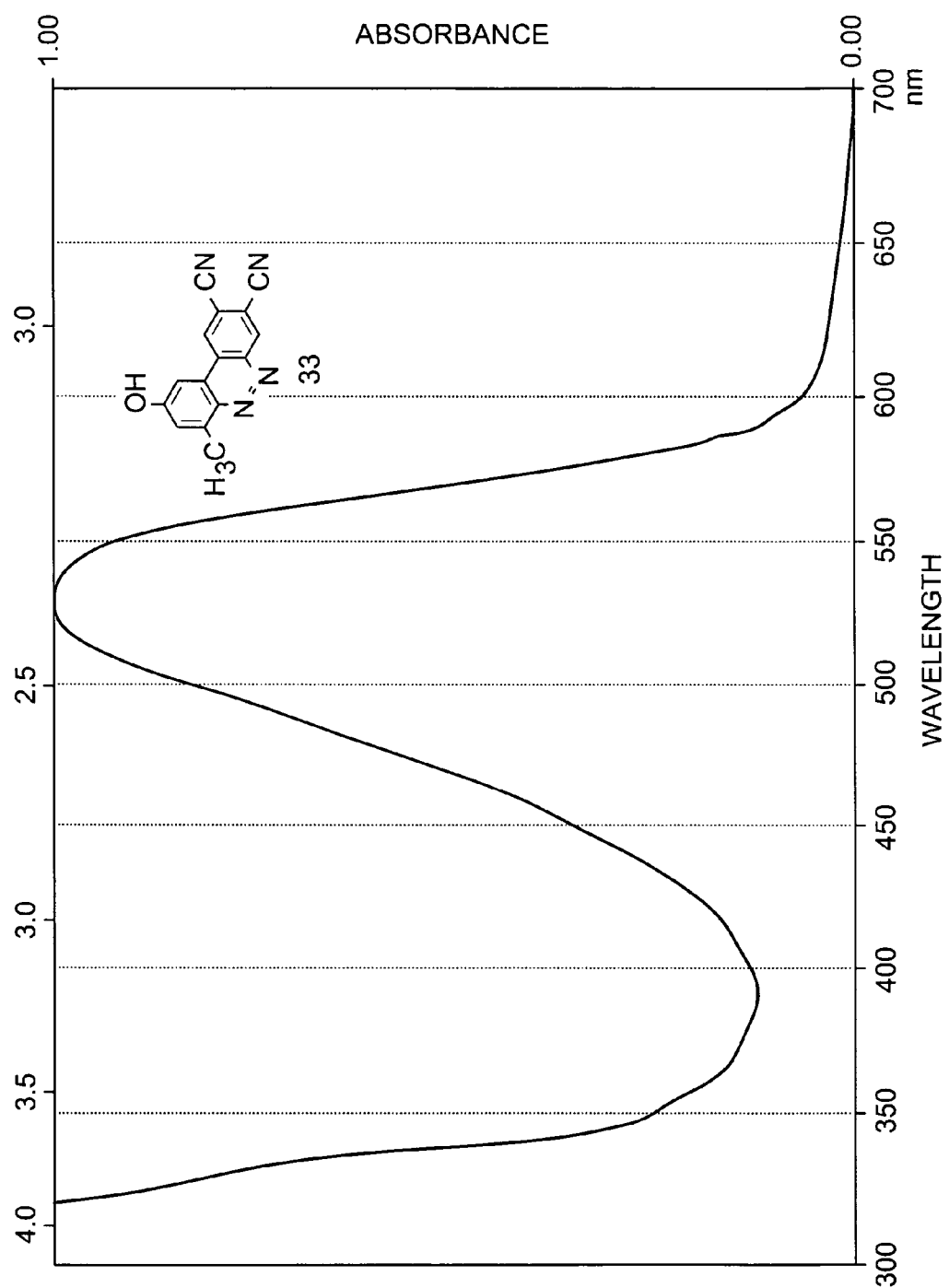
FIG. 3 is an absorption spectrum of Exemplified Compound 33 prepared in Example 3 (N,N-dimethylformamide as a solvent).

FIG. 3 shows an absorption spectrum of the thus-obtained Compound 33. As is apparent from FIG. 3, Compound 33 in a solution containing 3 drops of DBU in DMF had λmax of 525.9 nm, and εmax of $2.72 \times 10^4$ cm$^{-1}$M$^{-1}$.

The NMR spectrum of Compound 33 was as described below.

$^1$H NMR (300 MHz, DMSO-d$_6$) δ (ppm): 2.96 (3H, s), 2.96 (3H, s), 7.42 (1H,s), 7.85 (1H,s), 9.27 (1H,s), 2.53 (1H,s), 11.0 to 11.6 (1H, broad)

Further, a correlation between the following protons was confirmed in COSY and NOESY spectra. Therefore, the possibility that the thus-obtained product would be Compound 33' is denied, but it is identified that the thus-obtained product was Compound 33.

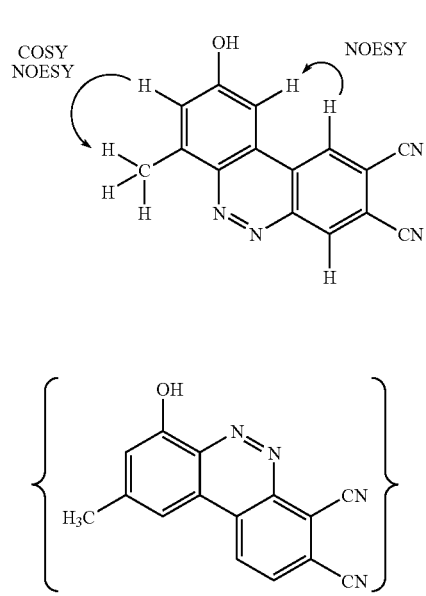

(Test Example)

A reduction test was performed through the following method.

Exemplified Compound 31 according to the present invention, or any one of Compounds for comparison A, B, and C shown below was mixed with 5 equivalents of sodium hydrosulfite in methanol-water, and the mixture was stirred at room temperature for 48 hours.

Compound for comparison A

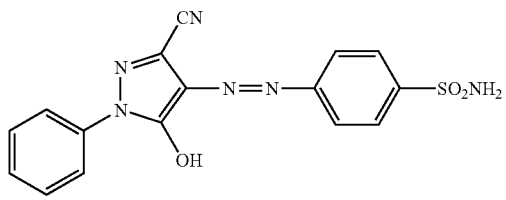

Compound for Comparison B

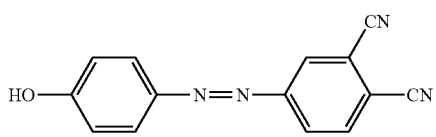

Compound for Comparison C

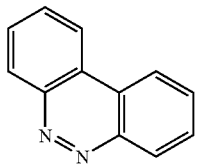

Analysis of each reaction liquid by LC/MS showed the following: In the reaction liquid from Compound for comparison A, 95% or more of Compound for comparison A disappeared, and Reduction products 1 and 2 were formed. Similarly, in the reaction liquid from Compound for comparison B, 95% or more of Compound for comparison B disappeared, and Reduction products 3 and 4 were formed. Contrary to the above cases, in the reaction liquid from Exemplified Compound 31 according to the present invention, 93% of Exemplified Compound 31 remained under the exactly same conditions, and decomposed products were produced in total of 7%, each of which was not one reduced at the azo group but one hydrolyzed at the cyano group. Further, in the reaction liquid from Compound for comparison C, 100% of Compound for comparison C also remained under the same conditions, but this compound showed no absorption in a visible region.

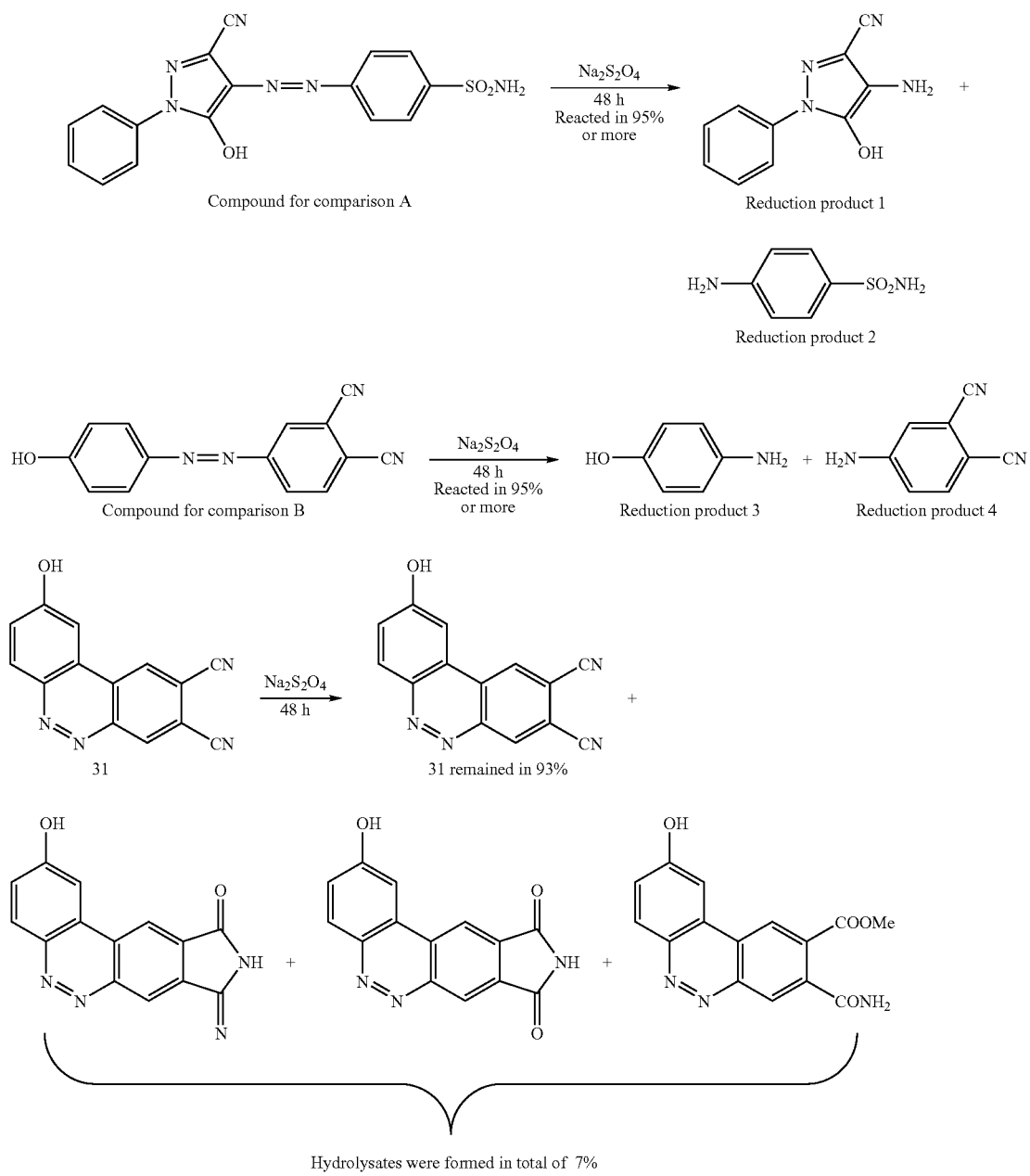

Further, upon exposure to S-9MIX, which is generally used as a metabolic enzyme for mutagenicity evaluation of a chemical substance, for 48 hours or more, it was confirmed that Compounds for comparison A and B were reduced, but Exemplified Compound 31 according to the present invention was not reduced.

The above-mentioned results apparently show that the compound of the present invention is remarkably highly-stable under reducing conditions.

Having described our invention as related to the present embodiments, it is our intention that the invention not be limited by any of the details of the description, unless otherwise specified, but rather be construed broadly within its spirit and scope as set out in the accompanying claims.

What we claim is:

1. A compound represented by formula (III):

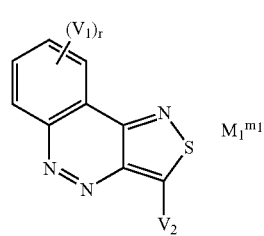

Formula (III)

wherein $V_1$ and $V_2$ each represent a substituent; the substituents $V_1$ and $V_2$ each represent a substituent represented by $W_1$ or $W_2$ described below; when at least one $V_1$ is a substituent represented by $W_1$, $V_2$ is a substituent represented by $W_2$, or when at least one $V_1$ is a substituent represented by $W_2$, $V_2$ is a substituent represented by $W_1$;

r represents 1 to 4;

$M_1$ represents a counter ion;

$m_1$ represents the number necessary for neutralizing charge;

$W_1$ represents a hydroxyl group, a primary, secondary or tertiary amino group, an acylamino group, or a sulfonamido group;

$W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the compound represented by formula (III) optionally has a substituent other than those represented by $V_1$ and $V_2$.

2. An azo dye comprising a compound represented by formula (III):

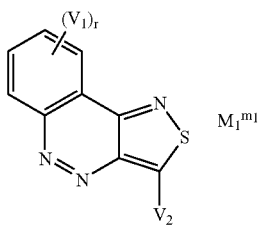

Formula (III)

wherein $V_1$ and $V_2$ each represent a substituent; the substituents $V_1$ and $V_2$ each represent a substituent represented by $W_1$ or $W_2$ described below; when at least one $V_1$ is a substituent represented by $W_1$, $V_2$ is a substituent represented by $W_2$, or when at least one $V_1$ is a substituent represented by $W_2$, $V_2$ is a substituent represented by $W_1$;

r represents 1 to 4;

$M_1$ represents a counter ion;

$m_1$ represents the number necessary for neutralizing charge;

$W_1$ represents a hydroxyl group, a primary, secondary or tertiary amino group, an acylamino group, or a sulfonamido group;

$W_2$ represents a nitro group, a cyano group, an alkoxycarbonyl group, an aryloxycarbonyl group, an alkyl- or aryl-sulfonyl group, a carbamoyl group, a sulfamoyl group, an alkenyl group, an alkynyl group, an aryl group, a heterocyclic group, a sulfo group, a carboxyl group, a heterocyclic oxy group, an ammonio group, an alkyl- or aryl-sulfinyl group, an alkyl- or aryl-sulfonyl group, an acyl group, or an aryl- or heterocyclic-azo group; and the compound represented by formula (III) optionally has a substituent other than those represented by $V_1$ and $V_2$.

3. The compound according to claim 1, wherein when at least one $V_1$ of Formula (III) is a substituent represented by $W_1$, said $W_1$ represents a hydroxyl group or a sulfonamido group.

4. The compound according to claim 3, wherein $V_2$ of Formula (III) is a substituent represented by $W_2$, and $W_2$ represents a cyano group, an alkyl- or aryl-sulfonyl group, or a sulfamoyl group.

5. The azo dye according to claim 2, wherein when at least one $V_1$ of Formula (III) is a substituent represented by $W_1$, said $W_1$ represents a hydroxyl group or a sulfonamido group.

6. The azo dye according to claim 5, wherein $V_2$ of Formula (III) is a substituent represented by $W_2$, and $W_2$ represents a cyano group, an alkyl- or aryl-sulfonyl group, or a sulfamoyl group.

* * * * *